(12) United States Patent
    Palmaz

(10) Patent No.:  US 12,661,221 B2
(45) Date of Patent:       Jun. 23, 2026

(54) METHODS OF MAKING VAVLULAR DEVICES

(71) Applicant: Vactronix Scientific, LLC, San Antonio, TX (US)

(72) Inventor: Julio C. Palmaz, Napa, CA (US)

(73) Assignee: Vactronix Scientific, LLC, San Antonio, TX (US)

( * ) Notice: Subject to any disclaimer, the term of this patent is extended or adjusted under 35 U.S.C. 154(b) by 0 days.

(21) Appl. No.: 19/278,211

(22) Filed: Jul. 23, 2025

(65) Prior Publication Data

US 2025/0359986 A1      Nov. 27, 2025

Related U.S. Application Data

(63) Continuation of application No. 19/035,408, filed on Jan. 23, 2025, now Pat. No. 12,370,041, which is a
(Continued)

(51) Int. Cl.
    *A61F 2/24*          (2006.01)
    *A61F 2/50*          (2006.01)

(52) U.S. Cl.
    CPC .......... *A61F 2/2415* (2013.01); *A61F 2/2418* (2013.01); *A61F 2/2469* (2013.01); *A61F 2002/5072* (2013.01)

(58) Field of Classification Search
    CPC .... A61F 2/2415; A61F 2/2418; A61F 2/2469; A61F 2002/5072
    See application file for complete search history.

(56) References Cited

U.S. PATENT DOCUMENTS

2003/0209835 A1*  11/2003  Chun ................... A61F 2/2412
                                                              264/339
2006/0047338 A1*   3/2006  Jenson ................. A61F 2/2412
                                                              623/2.11
(Continued)

FOREIGN PATENT DOCUMENTS

WO        2018035943 A1     3/2018
WO        2021086836 A1     5/2021

OTHER PUBLICATIONS

International Searching Authority; International Application No. PCT/US2023/01138913; Notification of Transmittal of the International Search Report and the Written Opinion of the International Searching Authority, or the Declaration; May 15, 2023.
(Continued)

*Primary Examiner* — Jerrah Edwards
*Assistant Examiner* — Aren Patel
(74) *Attorney, Agent, or Firm* — Rosenbaum IP, P.C.; David G. Rosenbaum

(57)                    ABSTRACT

A method of making a valvular medical device including a cell configured to flex out-of-plane upon application of a lateral or circumferential force applied to the biased cell, the biased cell having an elongate member projecting axially from an apex of the biased cell that flexes out-of-plane concomitantly with out-of-plane flexion of the biased cell. A monolithic hypotube is formed into a lattice structure having a plurality of biased cells and elongate members and is configured into a cardiac valve having a main body portion, a valve leaflet portion, and a plurality of elongate biasing arm members. A polymer coating or covering is disposed on the valve leaflet portion and the elongate biasing arm members and subtends space between adjacent pairs of elongate biasing arm members to form valve leaflet cusps
(Continued)

that are biased toward a central axis of the cardiac valve by the elongate biasing arm members.

20 Claims, 7 Drawing Sheets

Related U.S. Application Data continuation of application No. 18/058,464, filed on Nov. 23, 2022, now Pat. No. 12,220,312, which is a continuation of application No. 17/583,171, filed on Jan. 24, 2022, now Pat. No. 11,517,430.

(56)                    References Cited

U.S. PATENT DOCUMENTS

| | | | | |
|---|---|---|---|---|
| 2015/0282929 | A1* | 10/2015 | Rodriguez | C23C 14/24 |
| | | | | 427/2.25 |
| 2017/0165053 | A1 | 6/2017 | Buessler et al. | |
| 2019/0125558 | A1* | 5/2019 | Coyne | A61F 2/2412 |
| 2020/0188099 | A1* | 6/2020 | Dvorsky | A61F 2/9522 |
| 2023/0233317 | A1* | 7/2023 | Palmaz | A61F 2/90 |
| | | | | 623/1.26 |

OTHER PUBLICATIONS

International Searching Authority; International Application No. PCT/US2023/01138913; International Search Report; May 15, 2023.
International Searching Authority; International Application No. PCT/US/2023/01138913; Written Opinion of the International Searching Authority; May 15, 2023.

* cited by examiner

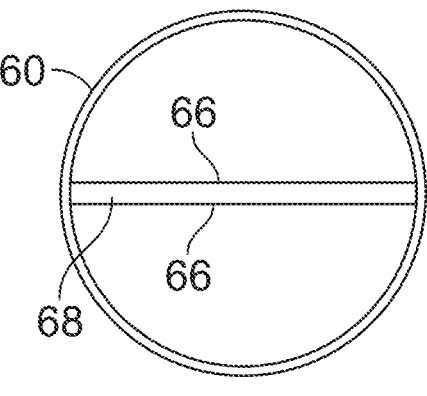
FIG. 9A
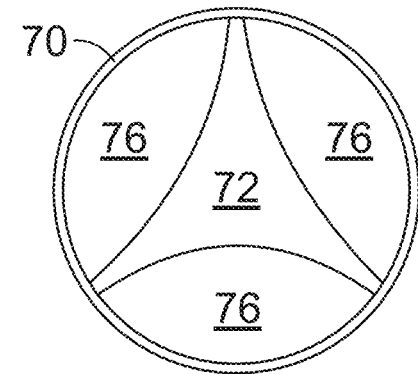
FIG. 9B
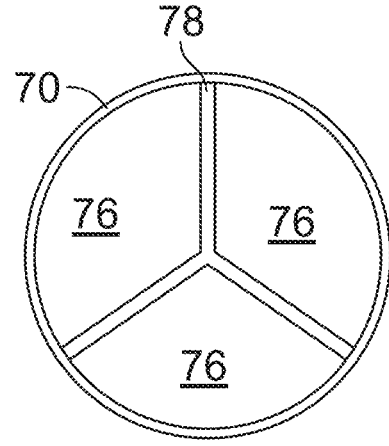
FIG. 10A
FIG. 10B
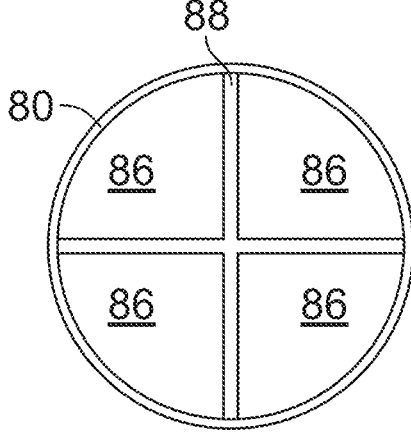
FIG. 11A
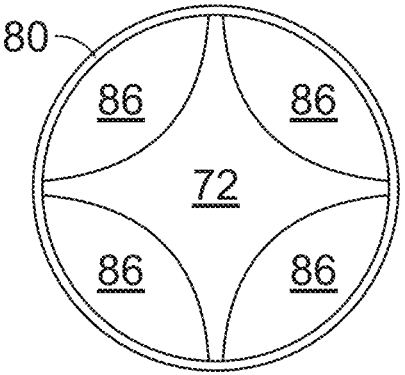
FIG. 11B

METHODS OF MAKING VAVLULAR DEVICES

CROSS-REFERENCE TO RELATED APPLICATIONS

This application is a continuation of co-pending U.S. patent application Ser. No. 19/035,408, filed Jan. 23, 2025, to issue as U.S. Pat. No. 12,370,041 on Jul. 29, 2025, which is a continuation of U.S. patent application Ser. No. 18/058, 464, filed Nov. 23, 2022, now U.S. Pat. No. 12,220,312 issued on Feb. 11, 2025, which is a continuation of U.S. patent application Ser. No. 17/583,171, filed Jan. 24, 2022, now U.S. Pat. No. 11,517,430 issued on Dec. 6, 2022.

BACKGROUND OF THE INVENTION

This disclosure pertains generally to biased cells that are configured to flex in- and out-of-plane upon application of a directional strain applied to the biased cell. More particularly, the present disclosure pertains to a biased cell configured to move in- and out-of-plane upon application of a compressive or expansive force to at least a portion of the biased cell. The in- and out-of-plane motion induced by application of a directional strain to the biased cell is capable, in turn, transferring the motive force from the biased cell to other structures joined, coupled, co-extensive, or communicating with the biased cell. One example of a structure that may be moved by the out-of-plane motion is a biasing arm coupled, joined, or integral with and project-ing from the biased cell. Out of plan motion of the biased cell will cause the biasing arm projecting from the biased cell to also move out-of-plane.

The present disclosure further includes devices that incor-porate one or more biased cells. Such devices include, for example, medical devices, such as steerable stents, cardiac valves, or orthopedic implants.

In one aspect of the present disclosure, the biased cell is a slot bounded by structural members, such a struts. Each biased cell is configured to assume a substantially quadri-lateral shape as a directional strain is applied to the biased cell. Each biased cell is bounded by a pair of first strut members defining a longitudinal axis of the biased cell and by a pair of second strut members, which may be substan-tially orthogonal to the first strut members and define opposing ends each biased cell. Each biased cell has a closed position in which the first and second strut members and the slot have a substantially quadrilateral cell shape. At least one spring strut is provided that extends along a longitudinal axis of the biased cell and is positioned between adjacent first strut members and between adjacent second strut members. The biased cell also has an open position in which the substantially quadrilateral cell deforms with the at least one spring strut extends along a diagonal between opposing included angles of the substantially quadrilateral cell. In this manner, when in the open position, the at least one spring strut divides the quadrilateral cell into triangles with the at least one spring strut forming a common hypotenuse of each triangle.

A force applied to opposing corners of the substantially quadrilateral cell having the spring strut extending from each opposing corner will cause flexion of the orthogonal corners not having the spring strut joined thereto, whereas a force applied to opposing corners of the substantially quad-rilateral cell not having the spring strut joined thereto will cause flexion of the orthogonal corners having the spring strut joined thereto. The applied forces may exert an expansive or a compressive force on the respective corners of the biased cell, which transfers the applied force to the spring strut, imparting a bending force to the spring strut, which, in turn, imparts out-of-plane flexion of sections of the biased cell.

In another variant of the present disclosure a biasing projection, which is contiguous with the spring strut, extends outwardly from a corner of the biased cell and a bending force, either externally applied or inherently applied, such as by shape memory or superelastic properties of the material employed for the biasing projection or the biased cell, transfers the bending force to the biased cell to either stabilize the biasing projection or enhance the bending moment of the biasing projection.

In a further variant of the disclosure, a transluminal cardiac valve is disclosed having a plurality of biased cells and biasing projections as part of and support for a valve leaflet apparatus configured to modulate valve leaflet open-ing and closing under the influence of cardiac muscle contraction and relaxation and pressure fluctuations across cardiac valves.

Hereinafter, all variants of biased cell of the present disclosure will be collectively referred to as a "biased cell" in the singular or plural.

Each biased cell may be combined with one or more other biased cells to form a larger set of biased cells. Each individual biased cell may be combined with other biased cells in such a manner as to have an additive or a subtractive quantum of flexion based upon the same applied force. That is, for example, a first biased cell unit may have an arbitrary quantum of flexion having a value of 1, a second biased cell unit may have an arbitrary quantum of flexion having a value of 1.5. Joining the first biased cell unit with the second biased cell unit will then yield an additive arbitrary quantum of flexion of 2.5 of the combined biased cell units. In distinction, joining a second biased cell unit having an arbitrary quantum of flexion having a value of 0.5 when combined with the first biased cell unit will yield a combined arbitrary quantum of flexion equal to 1.5. In this manner, the degree of flexion based upon a common force applied to a combination of biased cell units may be attenuated to either enhance or temper the overall degree of flexion of the combined biased cell units.

Each biased cell is configured as a substantially quadri-lateral cell defined by struts that bound the biased cell. Each of the struts are configurable to have either uniform or non-uniform dimensions such that variations in width, length, and/or thickness may exist with a single strut, from strut-to-strut within a biased cell, or from other individual biased cells. It will be appreciated that by providing such variations in width, length, and/or thickness, the net mechanical behavior of each biased cell will respond dif-ferently based upon the degree or positioning of such variations in width, length, and/or thickness of each indi-vidual frame biased cell.

As noted above, each biased cell further includes at least one spring strut extending along a diagonal between oppos-ing included angles of the biased cell. The spring strut may also have variations in width and/or thickness along a length of the spring strut. For example, the spring strut may have a width and/or thickness that tapers along its length either toward a mid-point along its length or toward each opposing end of the spring strut or along the build axis of the spring strut. Alternatively, the spring strut may have one or more curved sections, hinge regions, strain relief sections or the like, along its length to facilitate deflection of the spring strut either in-plane or out-of-plane relative to a normal axis of the spring strut upon application of an expansive or compressive force to the spring strut.

The biased cells of the present disclosure may have many different applications to impart flexion and/or directional movement of a larger structure into which the complaint biased cells are incorporated. For example, implantable cardiac valves intended for use in cardiac valve replacement and/or cardiac valve exclusion, may make advantageous use of the biased cells in forming part of the cardiac valve leaflet apparatus, such as a structural component of the cardiac valve leaflet, to modulate open and closing forces of the cardiac valve leaflets. As another example, the biased cells are capable of being incorporated into stents, such as intravascular or intraluminal stents, and assist in directional bending of the stent to facilitate wall apposition against anatomical luminal wall surfaces. A still further example of a use of the biased cell their incorporation into steerable catheters.

With particular reference to transluminal implantable cardiac valves, the biased cells of the present disclosure have particular utility as cardiac valve leaflet structural elements and valve leaflet roots, and/or as valve anchors. In particular, the present disclosure pertains to percutaneously deliverable, transluminal prosthetic cardiac valves capable of percutaneous delivery on low-profile catheters having 15 French size (hereinafter denoted "F") or less.

Contemporary transluminal cardiac valves are combinations of whole xenograft aortic valves or a metal frame and xenograft valve manufactured of equine, bovine or porcine pericardium. The xenograft valve leaflets are decellularized by lyophilization with tannin agents such as glutaraldehyde. These conventional valves require the use of large bore catheters in the range of 19-22 F (6.3-7.3 mm) diameter. Such large bore catheters are prohibitively large for people with relatively small femoral arteries, such as children or older people, and require alternative access approaches such as venous trans-septal, ventricular transapical, or via a temporary trans-subclavian arterial access graft. Xenografts have the potential risk of prion-vector transmission, such as Kreutzfeldt-Jakob disease. The decellularized protein frame is prone to become rigid and deformed with time and at least initially can be thrombogenic requiring oral anticoagulation. Xenograft valve tissue may also be the source of antigens inducing auto-immune disorder. Xenograft valve designs often involve a cusp motion-limiting portion of the valve that intrudes into the aortic root, caging the coronary ostia and limiting access to subsequent coronary interventions, if needed. Xenograft valves are, therefore, sub-optimal and elimination of animal tissue components in favor of synthetic valve leaflet materials is far more desirable.

By configuring the transluminal low-profile cardiac valve to be deliverable in a 15 F or less catheter, and having a polymer coating or covering associated with the biased cells, the cardiac valve of the present disclosure solves may of the present difficulties with both xenograft cardiac valves and synthetic leaflet cardiac valves.

SUMMARY OF THE INVENTION

It is an objective of the present disclosure to provide at least one biased cell configured to deform in- and out-of-plane and facilitate directional deflection of another structure into which the at least one biased cell is a portion thereof.

It is also an object of the present disclosure to provide a low-profile transluminal, i.e., 15 F or less, self-expanding cardiac valve incorporating the at least one biased cell configured to modulate valve leaflet deflection.

It is a further object of the present disclosure to provide a cardiac valve composed of a single piece superelastic metal frame forming the valve body and valve leaflet structure and having a polymer covering at least partially encapsulating or covering the valve leaflet structure.

It is yet another object of the present disclosure to provide a cardiac valve having a valve frame, including biasing projections that are configured as support structures for valve leaflets, are made of superelastic metal such as binary, ternary or quaternary nickel-titanium alloys and the valve leaflets are made of a biocompatible polymer.

It is still another object of the present disclosure wherein the binary, ternary or quaternary superelastic metal is fabricated by physical vapor deposition as a hypotube and then the valve frame and valve leaflet support structure are fabricated from the hypotube as a single, unitary and monolithic piece.

It is still a further object of the present invention to configure the valve frame and valve leaflet structure of the same superelastic material.

It is another further objective of the present disclosure that the valve frame and valve leaflet structure are made of different superelastic materials.

It is still another objective of the present disclosure to cover the valve leaflet structure with a polymer covering to form the valve leaflets.

It is yet another further object of the present disclosure that the cardiac valve leaflet structure exhibit chronic fatigue resistance equal to or greater than that exhibited by conventional xenograft cardiac valves.

It is still yet a further object of the present disclosure that the cardiac valve be capable of chronic repetitive cycles of at least 500 million cycles, preferably at least 1 billion cycles, without failure.

It is another objective of the present disclosure to provide a cardiac valve that is able to achieve the above fatigue profile at valve closing pressures exceeding 100 mm Hg present at the end of left ventricular systole and at lower pressures at the pulmonary, tricuspid and mitral valve positions.

It is still another objective of the present disclosure to provide a cardiac valve incorporating a biased cell in the cardiac valve that is configured to assist opening and/or closing of valve leaflets in the cardiac valve.

These and other objects, features, and advantages of the present disclosure will be more apparent to those skilled in the art from the following more detailed description of the monolithic transluminal cardiac valve which is capable of percutaneous deployment on a low profile catheter of 15 F or less.

BRIEF DESCRIPTION OF THE DRAWINGS

FIG. 9A is a top view of a bicuspid transluminal cardiac valve in a closed position in accordance with the present invention.

FIG. 9B is a top view of the bicuspid transluminal cardiac valve in an open position in accordance with the present invention.

FIG. 10A is a top view of a tricuspid transluminal cardiac valve in a closed position in accordance with the present invention.

FIG. 10B is a top view of the tricuspid transluminal cardiac valve in an open position in accordance with the present invention.

FIG. 11A is a top view of a quadricuspid transluminal cardiac valve in a closed position in accordance with the present invention.

FIG. 11B is a top view of the quadricuspid transluminal cardiac valve in an open position in accordance with the present invention.

DETAILED DESCRIPTION OF THE EMBODIMENTS

Figure 1:
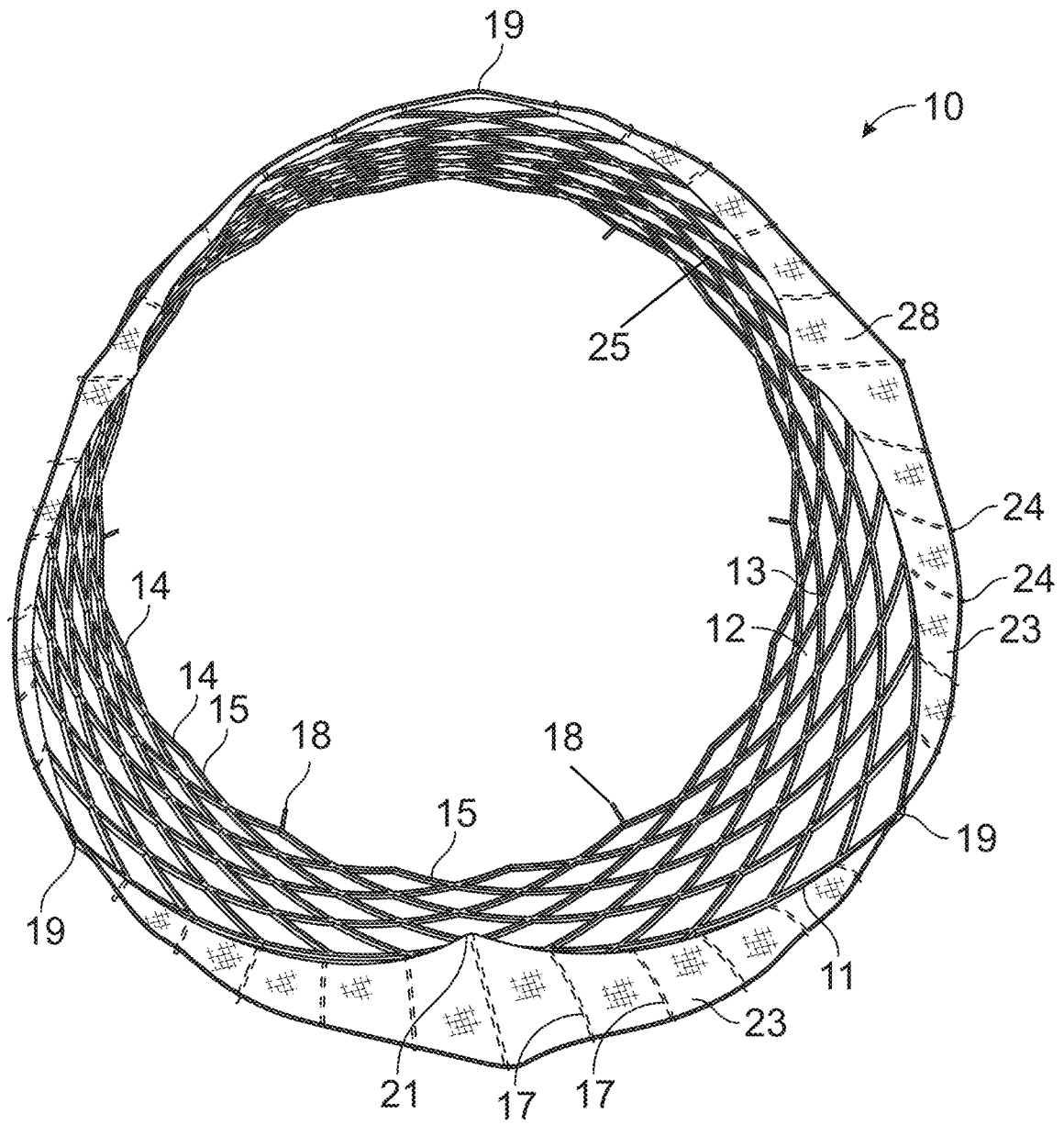
FIG. 1 is an end perspective view of a first variant of the transluminal cardiac valve in accordance with the present disclosure.

The terminology used herein is for the purpose of describing example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, cells, and/or components, but do not preclude the presence or addition of one or more other features, integers, steps, operations, cells, components, and/or groups thereof. The method steps, processes, and operations described herein are not to be construed as necessarily requiring their performance in the order discussed or illustrated, unless specifically identified as an order of performance. It is also to be understood that additional or alternative steps may be employed.

"Substantially" is intended to mean a quantity, property, or value that is present to a great or significant extent and less than, more than or equal to total. For example, "substantially vertical" may be less than, greater than, or equal to completely vertical.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

Recitation of ranges of values herein are merely intended to serve as a shorthand method of referring individually to each separate value falling within the recited range, unless otherwise indicated herein, and each separate value is incorporated into the specification as if it were individually recited herein.

References to "embodiment" or "variant", e.g., "one embodiment," "an embodiment," "example embodiment," "various embodiments," etc., may indicate that the embodiment(s) or variant(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment or variant, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The term "metal material" is intended to refer to metals, alloyed metals or pseudometals.

For purposes of this application, the terms "pseudometal" and "pseudometallic" are intended to mean materials which exhibit material characteristics substantially the same as metals. Examples of pseudometallic materials include, without limitation, composite materials, polymers, and ceramics. Composite materials are composed of a matrix material reinforced with any of a variety of fibers made from ceramics, metals, carbon, or polymers.

As used in this application the term "layer" is intended to mean a substantially uniform material limited by interfaces between it and adjacent other layers, substrate, or environment. The interface region between adjacent layers is an inhomogeneous region in which extensive thermodynamic parameters may change. Different layers are not necessarily characterized by different values of the extensive thermodynamic parameters but at the interface, there is a local change at least in some parameters. For example, the interface between two steel layers that are identical in composition and microstructure may be characterized by a high local concentration of grain boundaries due to an interruption of the film growth process. Thus, the interface between layers is not necessarily different in chemical composition if it is different in structure.

The term "build axis" or "build direction" is intended to refer to the deposition axis in the material. For example, as a material is being deposited onto a substrate, the thickness or Z-axis of the material being deposited will increase, this is the build axis of the material.

The terms "circumferential" or "circumferential axis" is intended to refer to the radial direction of a tubular, cylindrical or annular material or to the Y-axis of a polygonal material.

The terms "longitudinal," "longitudinal axis," or "tube axis" are intended to refer to an elongate aspect or axis of a material or to the X-axis of the material.

The term "film" is intended to encompass both thick and thin films and includes material layers, coatings and/or discrete materials regardless of the geometric configuration of the material.

The term "thick film" is intended to mean a film or a layer of a film having a thickness greater than 10 micrometers.

The term "thin film" is intended to mean a film or a layer of a film having a thickness less than or equal to 10 micrometers.

The term "supravalvular" is intended to mean above the cardiac valve, i.e., on the superior or cranial side of a valve.

The term "infravalvular" is intended to mean below the cardiac valve, i.e., on the inferior or caudal side of a valve.

This detailed description of exemplary embodiments makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not for purposes of limitation.

The cardiac valve 10 of the present invention is preferably made of a metal or pseudometal material fabricated as a single unitary hypotube. Preferably, the single unitary hypotube is formed by physical vapor deposition (PVD) of metal, metal alloy or pseudometal onto a substrate configured to form the precursor hypotube structure. Sputter deposition of either thick films or thin films is a preferred form of depositing the metal, metal alloy, or pseudometal to make the single unitary hypotube precursor for making the variants of the cardiac valve 10 according to the present invention. The deposited hypotube is then laser cut to form a lattice frame structure 12. The lattice frame structure 12 is configured to have a main body portion 25 including a plurality of biased cells 13, including spring struts 22, valve leaflet portions 24 including biasing projections 17, and, optionally, distal anchoring projections 18.

The main body portion 25, when diametrically expanded, is composed of first struts 14 that are helically oriented in a first circumferential direction along a longitudinal axis of the lattice frame structure 12 and second struts 15 that are helically oriented in a second circumferential direction along the longitudinal axis of the lattice frame structure 12. The first circumferential direction and the second circumferential direction may be opposing or offset from one and other such that the first struts 14 and the second struts 15 intersect to form biased cells 13 of the lattice frame structure 12. As with laser-cutting intravascular stents, the plurality of first struts 14 and the plurality of second struts 15 are formed cutting a plurality of slots in the hypotube precursor in a pattern such that the land areas between slots forms the plurality of first struts 14 and the plurality of second struts 15, respectively. A spring strut 22 is provided in the biased cells 13 within the lattice frame structure 12. Finally, the biasing projections 17 project longitudinally from at least some of the biased cells 13, preferably on a terminal row of biased cells at either or both a proximal and distal end of the lattice frame structure 12.

The lattice frame structure 12 is preferably made of a shape memory or superelastic metal material, such as, for example, binary, ternary, quaternary, or greater nickel-titanium based alloys. Examples of metal materials suitable for use in fabricating the lattice frame structure 12 are metal materials material is selected from the group consisting of titanium, vanadium, aluminum, nickel, tantalum, zirconium, chromium, silver, gold, silicon, magnesium, niobium, scandium, platinum, cobalt, palladium, manganese, molybdenum, hafnium, tungsten, rhenium, iridium, bismuth, iron, and alloys thereof, for example, nickel-titanium, nickel-titanium-cobalt, nickel-titanium-chromium, zirconium-titanium-tantalum alloys, or stainless steel. The foregoing metal materials are well-suited for physical vapor deposition to form the metal hypotube and tolerate post-deposition laser cutting and electropolishing to form the lattice frame structure 12, as well as subsequent shape setting of the valve leaflet portions 24, the main body portion 25, and/or distal anchor projections 18.

The valve leaflet portions 24 extends outward along a longitudinal axis of the main body portion 25. The valve leaflet portions 24 are co-extensive with the main body portion 25 of the lattice frame structure 12 and are formed by sections of the plurality of first struts 14 and the plurality of second struts 15. Alternatively, the valve leaflet portions 24 may be joined to the plurality of first struts 14 and/or the plurality of second struts 15, such as by welding or other means of joining known in the art. The valve leaflet portions 24 may have different constructs across the different variants of the cardiac valve of the present disclosure. For example, the valve leaflet portions 24 may have a plurality of biasing projections 17 extending distally from an end-most row of the main body portion 25 formed by the first struts 14 and the plurality of second struts 15. The biasing projections 17 are configured to support a polymer valve leaflet formed by a polymer covering over the biasing projections 17.

Each of the variants of the cardiac valve of the present disclosure are comprised generally of a main body portion 25 and a plurality of valve leaflet portions 24. The main body portion 24 of each variant is formed of a plurality of first struts 14 and plurality of second struts 15. The plurality of first struts 14 and the plurality of second struts 15 intersect one and other to form generally quadrilateral-shaped biased cells 13 of the main body portion 25. According to one example, the plurality of first struts 14 and the plurality of second struts 15 are defined by slot patterns formed in the precursor metal hypotube and have opposing helical orientations about a circumference of the main body portion 25. The main body portion 25 terminates, at one end thereof, in a generally sinusoidal or zig-zag configuration formed by the plurality of first struts 14 and the plurality of second struts 15 defining petal-like projections from the main body portion 25. At least two spaces are defined between adjacent pairs of the petal-like projections at the end of the main body portion 25 and are generally V- or U-shaped. Each of the petal-like projections and at least two of spaces 23 define a valve leaflet portion 24 of the cardiac valve 10.

The variants of the cardiac valve of the present disclosure differ in the construct or configuration of the valve leaflet portions 24. For example, the cardiac valve 10 in FIG. 1 has valve leaflet portions 24 that are at least partially formed by the plurality of first struts 14 and the plurality of second struts configured to form petal-like projections extending from an end of the main body portion 25. The valve leaflet portions 24 have a generally sinusoidal terminal end 11 having distal apices 19 and proximal apices 21. The sinusoidal terminal end 11 may simply be a relatively wider or thicker portion of a first strut 14 and/or a second strut 15 positioned at a most distal terminal end of the valve leaflet portion 24. The generally sinusoidal terminal end 11 and the valve leaflet portions 24 form the petal-like projections between the distal apices 19 and the proximal apices 21 that are spaced-apart from each other about a circumferential axis of the cardiac valve 10.

The plurality of biasing projections 17 extend along a longitudinal axis of the lattice frame structure 12 and project from an end row of cells in the lattice frame structure 12. The biasing projections 17 may project distally from the generally sinusoidal terminal end 11 of the valve leaflet portions 24 as illustrated in FIG. 1. Alternatively, the biasing projections 17 may intersect at least some of the biased cells 13 defined by the plurality of first struts 14 and the plurality of second struts 15 of the sinusoidal terminal end 11 row of the lattice frame structure 12. Optionally, biasing projections 17 are contiguous with the spring struts 22 and extend beyond the sinusoidal terminal end 11 of the lattice frame structure 12. In any of the foregoing described configurations, the biasing projections 17 are joined, coupled, integral with, and/or co-extensive with at least some of the biased cells 13 and are configured to move radially inward and outward toward a central axis of the cardiac valve 10 under at least partial influence of the biased cells 13 flexing.

Distal anchor projections 18 project distally from proximal apices 21 of the valve leaflet portions 24. The distal anchor projections 18 and/or the biasing projections 17 may have a width or a thickness that tapers along their length.

The distal anchor projections 18, the spring struts 22, and the biasing projections 17 may also be laser cut from the original hypotube or may be formed as separate components and either deposited onto the lattice frame structure 12 by physical vapor deposition or otherwise joined or coupled to the lattice frame structure 12.

Figure 2:
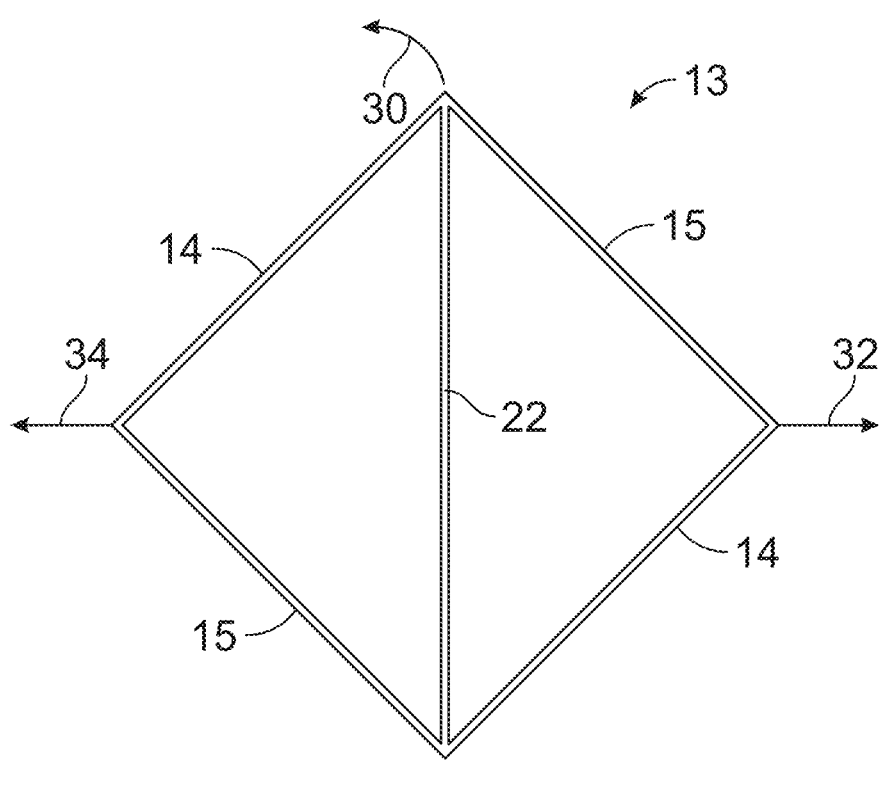
FIG. 2 is a planar view of a biased cell of a valve leaflet frame section of the transluminal cardiac valve in accordance with the present disclosure

FIG. 2 depicts a biased cell 13 showing an arrangement of the first struts 14 and second struts 15 defining four sides of and extending between the four sides of the biased cell 13 and a spring strut 22 extending diagonally between the included angles of opposing corners of the biased cell 13.

Upon application of a bending force 30 to a corner of biased cell 13, in which the spring strut 22 is present, such as by applying opposing forces 32, 34 to open corners of the biased cell, the biased cell 13 bends out-of-plane and, upon release of bending force 30 or opposing forces 32, 34, returns to the in-plane position. Both the bending force 30 and the opposing forces 32 represent the strain forces that will be applied to the cardiac valve 10 valve leaflets during operation of the valves once implanted. The out-of-plane flexion bending of the biased cell 13 of valve leaflet 24 and recovery of the bending serves to ensure apposition of valve leaflets 24 during valve closure and mechanical support for the valve leaflet 24 during both valve opening and closure.

Upon application of opposing forces 32, 34 orthogonal to a longitudinal axis of spring strut 22 the apices of the biased cell 13 exert a compressive force onto the spring strut 22, which then flexes under the influence of the compressive force and allows the biased cell 13 to flex out-of-plane. Out-of-plane flexion of the biased cell 13, in turn, transfers a motive force to the biasing projection 17 (not shown) causing the biasing projection to deflect inward toward the central opening of the cardiac valve 10.

As shown in FIG. 1, a polymer covering or coating is provided on the valve leaflet portions 24 that subtends the space between pairs of distal apices 19 and covers circumferentially adjacent petal-like projections of the valve leaflet portions 24. In this manner, the valve leaflet portions 24 are embedded in, covered by, or coated with a coherent polymer material that acts as valve leaflets for the cardiac valve 10.

The polymer covering 28 also covers to covers the biasing projections 17 projecting from the sinusoidal terminal end 11 of the valve leaflets portions 24 and subtends the spaces 23 between adjacent pairs of the biasing projections 17. The polymer covering 28 is employed to both form the valve leaflets and achieve valve competency without backflow blood leakage or regurgitation. The basic properties of the desirable polymer include: 1) low thrombogenicity; 2) fatigue resistance; 3) high material strength allowing for thin coating or covering of the first struts 14, second struts 15, biasing projections 17, as well as the distal anchor projections 18, while providing a webbing that subtends open space between the foregoing; and 4) high adhesion strength to the lattice frame structure 12. The polymer is preferably an elastomer that is configured to accommodate conformational changes of the valve leaflet sections 24 during valve opening and/or closing. Flexible non-elastomeric polymers may be employed provided that they have sufficient pliability, conformability, and fatigue resistance to function as valve leaflets at small material thicknesses. A wide variety of biocompatible polymers may be used as the embedding polymer for the valve leaflets. For example, polytetrafluoroethylene (PTFE), urethanes, such as polyurethane, poly (styrene-b-isobutylene-b-styrene (SIBS), poly (D, L-lactic acid) (PLA) and/or poly (D, L-lactic-co-glycolic acid) (PLGA), and/or polyimides, such as poly (4,4'-oxydiphenylene-pyromellitimide (KAPTON, E.I. du Pont de Nemours and Company, Wilmington, Delaware) may be useful as the polymer for the valve leaflets in the transluminal cardiac valve of the present invention.

The polymer may be applied by a wide variety of methods, depending upon the polymer selected, such as, for example, by dip coating, spraying, electrospinning, sintering, or vapor deposition, among other methods. Microporous microstructures in the polymer may be created, such as by electrospinning or by expansion of PTFE to expanded PTFE (ePTFE) prior to covering the cardiac valve.

Microporous microstructures in the polymer covering may be provided to enhance protein and cellular adhesion to the polymer. Enhanced protein and/or cellular adhesion to the valve leaflets and/or other portions of the cardiac valve may also be achieved by other methods, such as by texturing, surface charge manipulation, or the like.

The lattice frame structure 12 is preferably made of bare-metal to achieve adequate anchoring against and exclusion of the compressed native valve by pillowing effect. Both the anchoring and exclusion of the native valve may be complemented by other securing features on the lattice frame structure 12, such as barbs (not shown). The proximal end of the main body portion 25 may include one or more anchoring projections 221 (shown in FIGS. 12A, 12B, 13 and 15) that project from the proximal end of the main body portion 25 and may be shape-set to flare radially outward and open toward the atrial or ventricular outflow to facilitate blood flow from the atrium or ventricle and into and through the cardiac valve 10. This proximal flare is also useful during deployment to stabilize the valve during a retrograde femoral approach during implantation. Further anchoring above the valve plane may also be achieved by providing anchoring projections originating at commissures between adjacent valve leaflet sections 24 that are shape set to project radially or circumferentially outward away from a central longitudinal axis of the cardiac valve 10.

Figures 3, 4, 5, 6, 7A, 7B, 8:
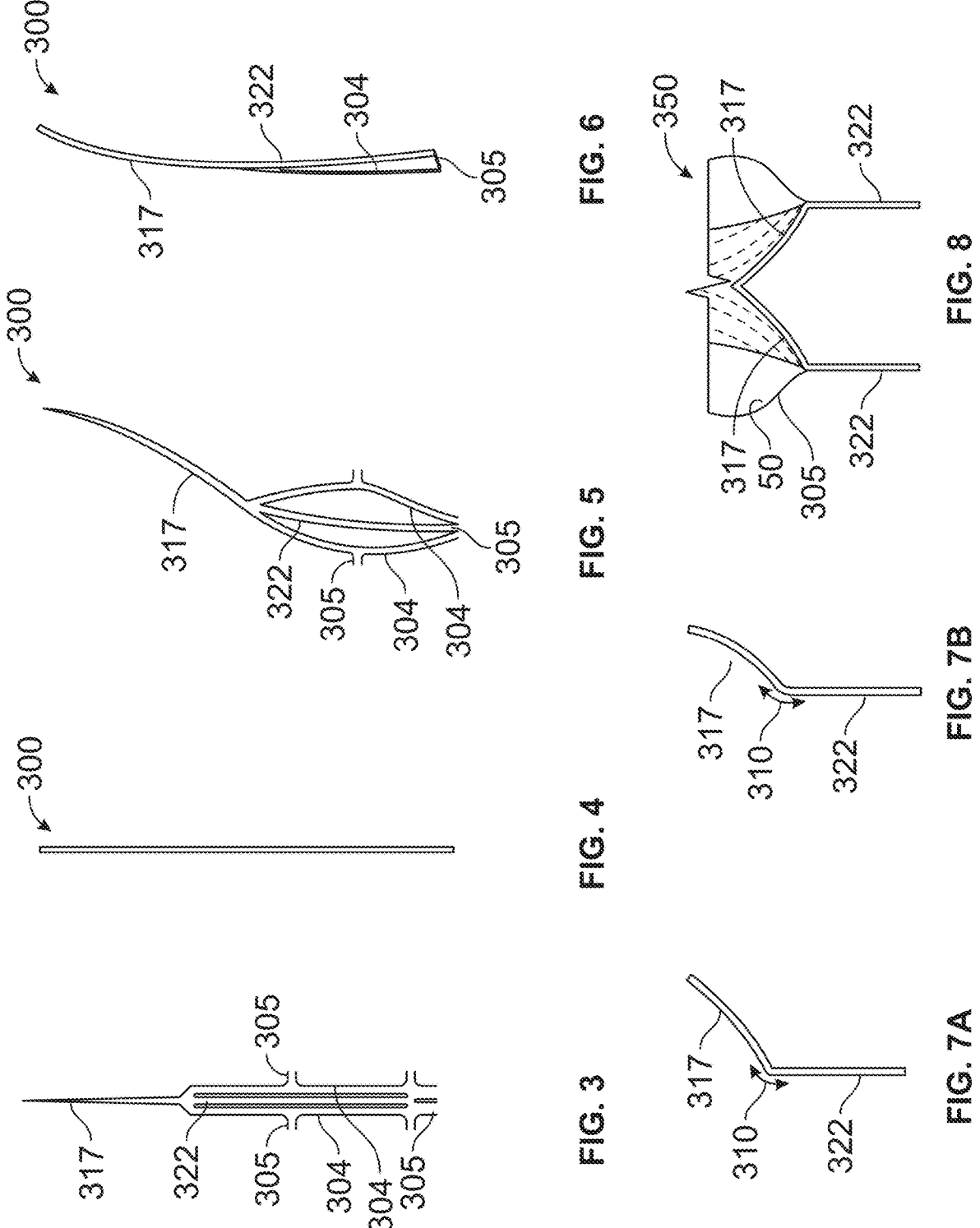
FIG. 3 is a diagrammatic plan view of a biased cell and biasing projection in an unstrained state.
FIG. 4 is a diagrammatic side elevational view of the biased cell and biasing projection in the unstrained state.
FIG. 5 is a diagrammatic plan view of the biased cell and biasing projection in a strained state.
FIG. 6 is a diagrammatic side elevational view of a biased cell and biasing projection in its strained state.
FIG. 7A is a diagrammatic side elevational view showing deflection of the biasing projection.
FIG. 7B is a diagrammatic side elevational view showing deflection recovery of the biasing projection.
FIG. 8 is a diagrammatic side elevational view of a valve and valve leaflets in a closed position in accordance with the present disclosure.

FIG. 3 is a diagrammatic plan view of a biased cell 300. Biased cell 300, like biased cell 13, is bounded by a pair of first strut members 304 and second strut members 305 and has a spring strut 322 extending longitudinally between the second strut member 305 and positioned intermediate between a pair of first strut members 304. The spring strut 322 projects outward from the biased cell 300 along a longitudinal axis thereof. Like biased cell 13, biased cell 300 is formed of a unitary, monolithic hypotube that is machined, such as by laser cutting, with a plurality of slots defining the first strut members 304, the second strut members 305 and the spring strut 322. The hypotube may be made of shape memory, superelastic or plastically deformable, i.e., balloon expandable materials, as discussed below.

FIG. 4 is a diagrammatic side elevational view of the biased cell 300 in a planar unstrained state where no lateral, in the case of a planar lattice structure, or circumferential, in the case of a tubular lattice structure, force is applied to the biased cell 300.

FIG. 5 is a diagrammatic plan view of the biased cell 300 illustrating expansion of the biased cell 300 as a result of a lateral force applied to the second strut members 305 causing the first strut members to open to a diamond shape while exerting an axially compressive strain to that part of the spring strut 322 that extends between the second strut members 305. As shown in FIG. 9, the axially compressive strain exerted on spring strut 322, causes the biased cell 300 to deform out-of-plane and the portion of spring strut 322 that projects longitudinally from biased cell 300 deforms out-of-plane as well.

The out-of-plane deflection of the projecting portion of spring strut 322 is advantageously employed in the case of a valve leaflet to act as a spring strut as shown in FIGS. 7A and 7B wherein the spring strut portion of spring strut 322 angularly deflects 310 from the longitudinal axis of the biased cell 300. When employed as a valve leaflet spring strut, a polymer covering 350 extends between a plurality of spring struts to form the valve leaflet. The polymer covering 350, as shown in FIG. 8, forming the valve leaflets opens and closes under the influence of both the blood pressure gradient across the valve, and the spring strut portion of the spring strut 322.

The spring strut 322, when fabricated of a shape memory or superelastic material, is capable of shape setting to form the curvature of the valve leaflets and program the amplitude of deflection of the spring strut portion of the spring strut 322. Similarly, the spring strut 322 can be formed to have one or more tapers or have one or more strain relief sections that will modulate the amplitude of deflection of the spring strut portion of the spring strut 322 as well as positively affect its fatigue resistance.

FIGS. 9A and 9B illustrate a bicuspid cardiac valve 60 in accordance with the present invention. FIG. 9A depicts the valve leaflets 66 in a closed position with the distal ends of each valve leaflet 66 in apposition with each other. FIG. 9B illustrates the valve leaflets 66 in their open position creating a generally elliptical blood flow opening 62 that allows blood flow through the bicuspid cardiac valve 60.

FIGS. 10A and 10B illustrate a tricuspid cardiac valve 70 in accordance with the present invention. FIG. 10A depicts the valve leaflets 76 in a closed position with the distal ends of each valve leaflet 76 in apposition with each other. FIG. 10B illustrates the valve leaflets 76 in their open position creating a generally three-sided hypocycloid blood flow opening 72 that allows blood flow through the tricuspid cardiac valve 70.

FIGS. 11A and 11B illustrate a quadricuspid cardiac valve 80 in accordance with the present invention. FIG. 11A depicts the valve leaflets 86 in a closed position with the distal ends of each valve leaflet 86 in apposition with another valve leaflet 86. FIG. 11B illustrates the valve leaflets 86 in their open position creating a generally four sided hypocycloid blood flow opening 82 that allows blood flow through the quadricuspid cardiac valve 80.

Figures 12A, 12B:
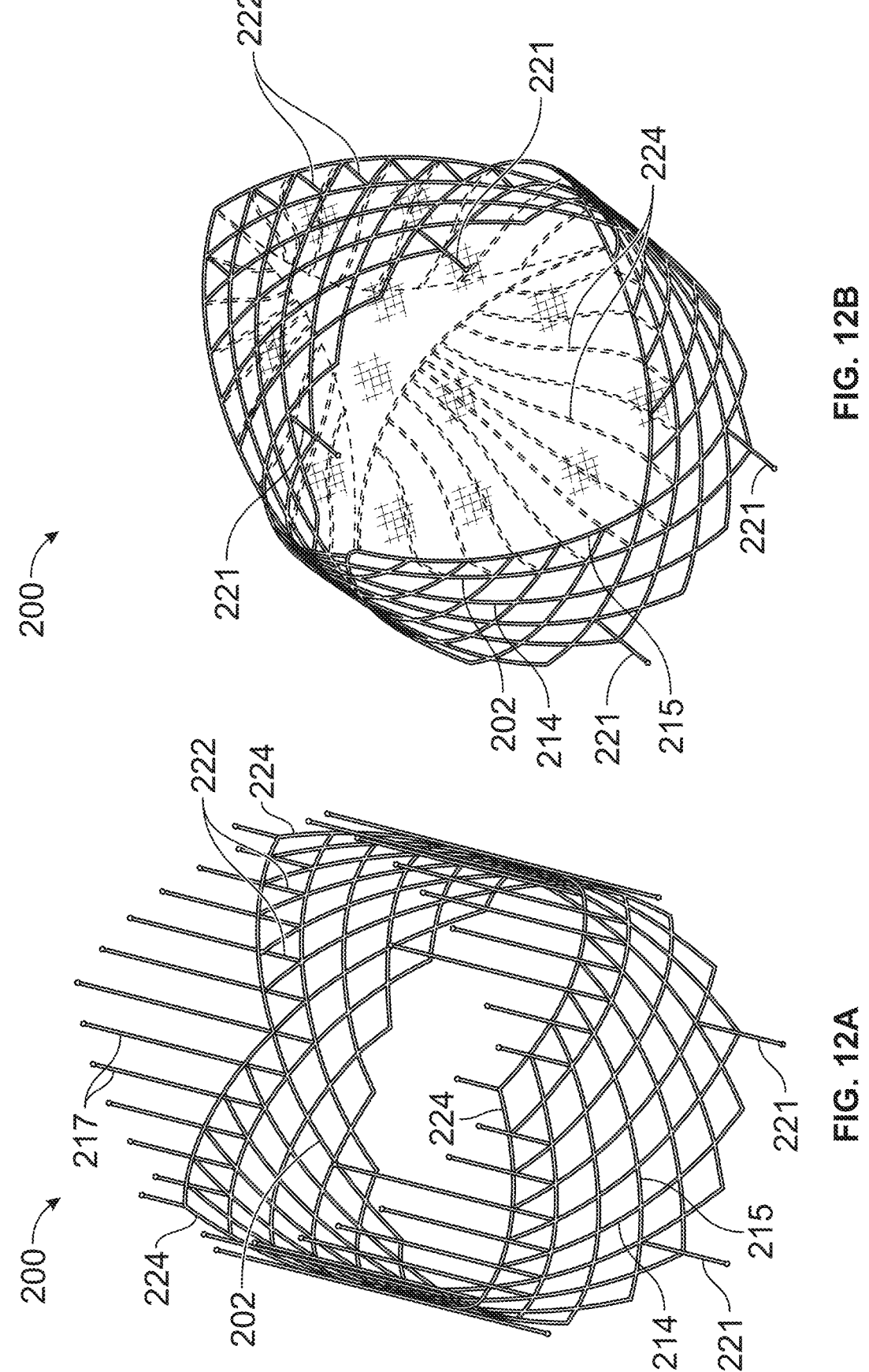
FIG. 12A is a first end perspective view of the transluminal cardiac valve structure without polymer covering on the biasing projections.
FIG. 12B is a second end perspective view of the transluminal cardiac valve structure with a polymer covering on the biasing projections.

FIG. 12A and FIG. 12B, illustrate an infra-valvular perspective view and a supra-valvular perspective view of the cardiac valve 200, respectively, showing a tricuspid valve embodiment as represented by three petal-like valve leaflet sections about the circumference of cardiac valve 200. It will be understood that a bicuspid variant of the cardiac valve 200 would have two diametrically opposing petal-like valve leaflet sections about the circumference of the cardiac valve, whereas a quadricuspid variant of the cardiac valve 200 would have four petal-like valve leaflet sections about the circumference of the cardiac valve.

Each of the anchoring projections 221 and/or the distal anchor projections 18 may have a rounded distal or proximal terminus onto which a radiopaque marker may be swaged or otherwise joined or applied. By providing radiopaque markers at the rounded distal or proximal terminus, the proximal and distal aspects of the cardiac valve 10 will be visible under fluoroscopy during implantation of the cardiac valve 10. Alternatively, or in addition, all or a portion of each anchoring projection 221, distal anchor projections 18, and/or the first struts 14, second struts 15 and/or biasing projections 172 may have a radiopaque material formed therein or thereupon as part of the vacuum deposition process to make the metal material hypotube. An example of selective deposition of radiopaque marker materials onto regions of a tubular hypotube is disclosed in co-pending, commonly assigned U.S. patent application Ser. No. 17/327,667 filed May 21, 2021, which is hereby incorporated by reference in its entirety.

Figure 13:
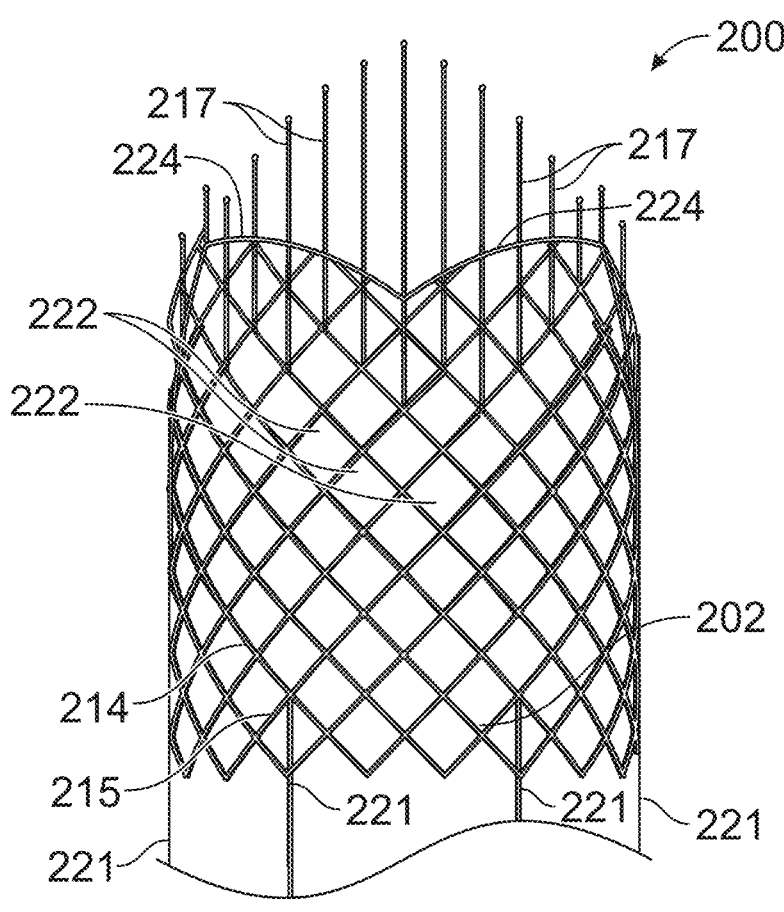
FIG. 13 is a side elevational view of a transluminal cardiac valve without a polymer covering on the valve leaflets.
Figure 14:
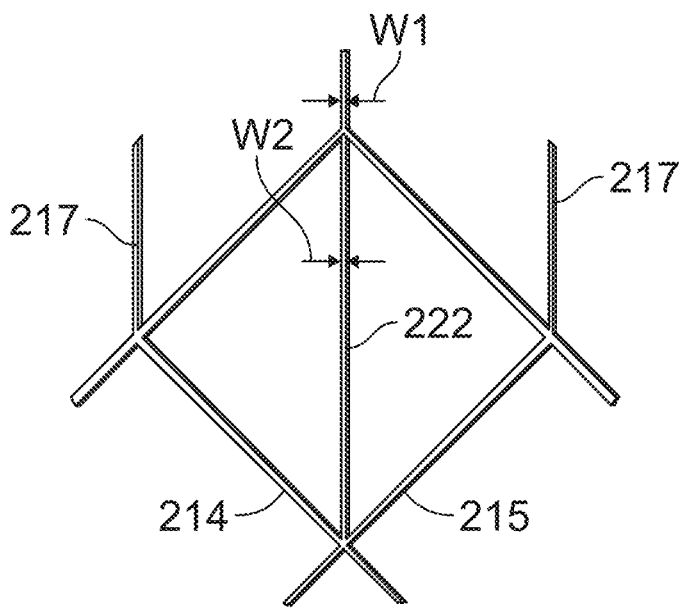
FIG. 14 is a fragmentary plan view of a biased cell and biasing projections in accordance with the present disclosure.

FIG. 13 is a side elevational view of cardiac valve 200 without the polymer coating of covering 250 showing the petal-like shape of the valve leaflet portions 224 and the corresponding petal-like shape of the collective biasing projections 217. FIG. 14 provides an enlarged view of a biased cell having biasing projections 217 and spring strut 222. Each of the spring strut 222 and the biasing projections 221 have a width W2 and W1, respectively, that may be the same width or different widths. For example, a portion of the biasing projection 217 that extends from biased cell 203 may have a narrower or greater width W1 than a width W2 of the spring strut 222.

Figure 15:
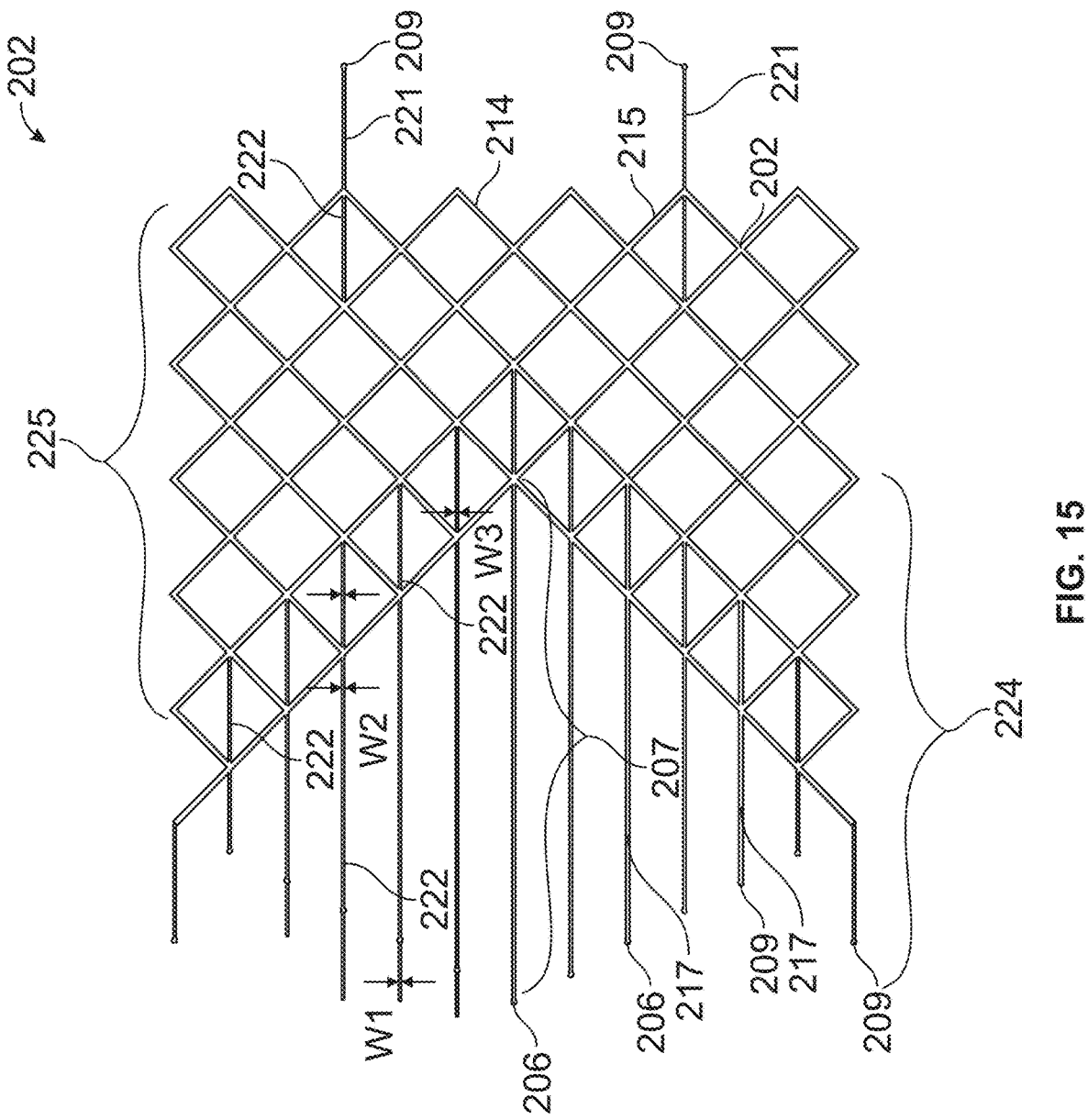
FIG. 15 is a plan view of a section of the single valve leaflet section of the transluminal cardiac valve in accordance with the present disclosure.

FIG. 15 is a planar view of a one-third circumferential section of the lattice frame structure 202 for a tricuspid cardiac valve in accordance with an alternative embodiment of the cardiac valve 200 present invention. Lattice frame structure 202, like lattice frame structure 12 described above, is composed of a plurality of first struts 214, a plurality of second struts 215, spring struts 222, a plurality of biasing projections 217, and anchor projections 221. The plurality of the first struts 214 have a helical orientation in a first direction relative to the longitudinal and circumferential axes of the cardiac valve 200 and the plurality of second struts 215 have a helical orientation in a second direction relative to the longitudinal and circumferential axes of the cardiac valve 200. The first direction and the second direction may be opposing or offset from one and other such that the first struts 214 and the second struts 215 intersect to form the biased cells 203 of the lattice frame structure 202, as exemplified in detail in FIG. 15.

Lattice frame structure 12, 202 is made of a shape memory or superelastic metal material, such as, for example, binary, ternary, quaternary, or greater nickel-titanium based alloys. Alternatively, lattice frame structure 202 is made of a plastically deformable, e.g., balloon expandable metal material, where the spring struts 222 and biasing projections 217 are elastic. Examples of metal materials suitable for use in fabricating the lattice frame structure 12, 202 are metal materials material is selected from the group consisting of titanium, vanadium, aluminum, nickel, tantalum, zirconium, chromium, silver, gold, silicon, magnesium, niobium, scandium, platinum, cobalt, palladium, manganese, molybdenum, hafnium, tungsten, rhenium, iridium, bismuth, iron, and alloys thereof, for example, nickel-titanium, nickel-titanium-cobalt, nickel-titanium-chromium, zirconium-titanium-tantalum alloys, or stainless steel. The foregoing metal materials are suited for physical vapor deposition to form the metal hypotube and tolerate post-deposition laser cutting and electropolishing to form the lattice frame structure 202.

The plurality of biasing projections 217 may originate at an apex of a biased cell 203 and project distally from a distal end of the valve leaflet portion 224. Each of the plurality of biasing projections 217 are be in longitudinal alignment with a spring strut 222 and contiguous therewith. The plurality of biasing projections 217 each have a distal end 206 that may, optionally, terminate in a rounded end 209 configured to accept a radiopaque marker (not shown) coupled thereto. The plurality of biasing projections 217, optionally, each have different lengths 207 such that the distal end 206 of the plurality of biasing projections 217 align to form a generally sinusoidal distal end of the cardiac valve 200. This generally sinusoidal distal end of the cardiac valve 200 functions to support a polymer coating or covering 250 illustrated in FIG. 16 that forms the valve leaflets of the cardiac valve 200.

Each of the plurality of biasing projections 217 may, optionally, have a tapered width that tapers to a relatively smaller width W2 distally that relatively larger width W1 at proximal aspects of each of the plurality of elongate members 108 that emanate from a first strut 214 or a second strut 215 at a terminal end of the lattice frame structure 202. For example, W2 may be 0.06 mm whereas W2 may be 0.1 mm. Also optionally, the width of each of the plurality of biasing projections 217 may taper to a smaller width W3 where the spring strut 222 bisects a biased cell 203. The length, width, and optional taper of each of the plurality of biasing projections 217 may be selected based upon the desired configuration of the valve leaflet configuration, the polymer selected for the coating or covering 250, and the opening and closing pressures desired for the valve leaflets. Finally, the biasing projections 217 may have a taper along the build axis of the biasing projections 217.

The plurality of anchoring projections 221 may, optionally, also be provided at one or both ends of the body portion 225 of the lattice frame structure. The plurality of anchoring projections 221 project proximally from the cardiac valve 200 and also bisect a proximal terminal end of the biased cell 203. Like each of the biasing projections 217, the anchoring projections 221 may, optionally, have a rounded end 212 configured to couple to a radiopaque marker (not shown).

In use, the cardiac valve 10, 200 is collapsed to a smaller diametric profile and loaded into a restraining delivery tube of a delivery catheter. As noted above, the geometry of cardiac valve 10 and/or cardiac valve 200 allow for the smaller diametric profile to be loaded into a catheter having a 15 F inner diameter of less and 16 French outer diameter of less. Most preferably the delivery catheter will have a 13-15 French inner diameter (4.3 to 5 mm) and a 14-16 French outer diameter (4.67 to 5.3 mm). The deployed diameter of a cardiac valve 10 or cardiac valve 200 in the aorta will be between 30 mm or larger depending upon the patient. Therefore the single tubular design of the cardiac valve 10, 200 has an 8-10 fold factor of diametric expansion.

It will be appreciated by those skilled in the art that selection of superelastic alloys with greater material properties that nitinol may also allow for PVD fabrication of the cardiac valves 10, 200 that are capable of even smaller collapsed smaller diameters and allow for even smaller delivery catheter profiles.

As the cardiac valve 10, 200 exits the restraining delivery tube, the lattice frame structure 12, 202 will diametrically expand and the valve leaflet sections 24 will deform radially inward toward the central axis of the cardiac valve 10, 200 all following a pre-determined heat-set configuration. The heat set configuration is the resting position of the valve leaflets and is induced by a bias imposed on polymer valve leaflets by the distal anchor projections 18, 208 such that the free distal edges of the valve leaflets meet and abut in a commissure in the center of the cardiac valve 10, 200. Diametric expansion of the lattice frame structure 12, 202 causes the circumferential expansion of the biased cells 13, 203. The the spring struts 22 also limit a shortening effect induced by the circumferential expansion of the biased cells 13, 203.

It will be appreciated that a bicuspid, tricuspid or quadricuspid design of the cardiac valve 10, 200 will require differing lengths of the anchoring projections 18, 221 and the valve leaflet portions 24, 224. For example, since a quadricuspid design has four cusps, each cusp may have a relatively lesser length than a tricuspid or bicuspid valve design. Where a shorter length of each cusp is possible, the mechanical load on the anchoring projections 18, 221 and the valve leaflet portions 24, 224 will be reduced and the length and/or number of distal anchor projections 18, 208 may be adjusted in view of a smaller load applied by the individual valve leaflets.

While the invention has been described with reference to its preferred embodiments, those of ordinary skill in the relevant arts will understand and appreciate that the present invention is not limited to the recited preferred embodiments, but that various modifications in material selection, deposition methodology, manner of controlling the grain formation within individual layers, across multiple layers, or throughout the entire thickness of the multi-layer material, and deposition process parameters may be employed without departing from the invention, which is to be limited only by the claims appended hereto.

The invention claimed is:

1. A method of making a valvular medical device, comprising the steps of:

Physical vapor depositing at least one of a biocompatible metal, metal alloy, or pseudometal onto a cylindrical deposition substrate and forming a precursor deposited material;

forming a lattice structure in the precursor deposited material, the lattice structure having a valvular end, the valvular end having a plurality of biased cells, each of the plurality of biased cells having a spring strut, and a biasing projection projecting from a first end therefrom;

removing the lattice structure from the substrate;

providing a polymer covering spanning a space between the biasing projections thereby forming valve leaflets of the valvular medical device.

2. The method of claim 1, wherein the valvular medical device is configured to have a delivery profile less than or equal to 15 French.

3. The method of claim 1, wherein the step of forming the lattice structure further comprises the step of forming the plurality of biased cells in an end frow of cells in the lattice structure, wherein at least some of the plurality of biasing projections project from an apex of at least some of the end row of cells in the lattice structure.

4. The method of claim 1, wherein the step of providing a polymer covering further comprises the step of extending the polymer covering between each of the biasing projections and forming at least two leaflets of the valvular medical device.

5. The method of claim 4, further comprising the step of forming commissures between the at least two valve leaflets.

6. The method of claim 4, further comprising the step of configuring the polymer covering to share a mechanical load with at least one of the plurality of biasing projections and at least one of the biased cells.

7. The method of claim 4, wherein the step of forming a lattice structure further comprises the step of forming a spring strut member extending diagonally within each of the plurality of biased cells.

8. The method of claim 4, further comprising the step of configuring at least one biasing projection as a structural support for each of at least two valve leaflets.

9. The method of claim 1, wherein the step of forming a lattice structure further comprises forming a tubular lattice structure having undulating sections at an end of the tubular lattice structure and arraying each of the undulating sections to be adjacent to each other about a circumference of the end of the tubular latticed structure.

10. The method of claim 1, wherein the step of forming a pattern of a lattice structure further comprises the step of forming a plurality of anchor projections projecting from a second end of the lattice structure.

11. The method of claim 10, further comprising the step of configuring the plurality of anchor projections to deflect radially outward such that the plurality of anchoring projections are capable of anchoring the latticed structure to an anatomic valvular annulus.

12. The method of claim 1, wherein the step of forming a pattern of a lattice structure in the hypotube further comprises the step of monolithically forming the plurality of biased cells having a spring strut and the biasing projections with the latticed structure.

13. The method of claim 1, wherein the step of forming a pattern of a lattice structure i further comprises the step of forming at least some of the biasing projections with a taper along a length thereof.

14. The method of claim 1, wherein the step of forming a pattern of a lattice structure further comprises the step of forming rounded distal ends on each of the biasing projections.

15. The method of claim 1, further comprising the step of shape setting at least some of the biasing projections to deflect the polymer covering both toward and away from the central longitudinal axis of the lattice structure.

16. The method of claim 1, wherein the step of forming a pattern of a lattice tubular structure further comprises the step of forming at least two valve leaflets to be in apposition with one another when the valvular medical device is in a closed position.

17. A method of making a transluminal cardiac valve, comprising the steps of:

forming a hypotube by physical vapor deposition of a biocompatible metal, metal alloy or pseudometal onto a substrate;

forming a pattern of a lattice tubular structure in the hypotube, the lattice tubular structure having a valvular end and an anchoring end thereof, the valvular end having a plurality of biased cells at the valvular end and biasing projections extending from the biased cells, wherein the tubular latticed structure further comprises a plurality of slots that open upon diametric expansion of the tubular latticed structure and define a plurality of helically oriented struts in the tubular lattice structure;

removing the pattern of the lattice tubular structure from the hypotube and substrate;

providing a polymer covering spanning at least some of the biasing projections and spanning spaces between the biasing projections thereby forming a plurality of valve leaflets, each of the plurality of valve leaflets being configured to move both toward and away from a central longitudinal axis of the tubular latticed structure.

18. The method of claim 17, wherein the valvular end of the lattice tubular structure is configured to have a substantially sinusoidal shape.

19. The method of claim 17, wherein the step of forming a pattern of a lattice tubular structure further comprises the step of forming at least one spring strut in each of the biased cells of the pattern of the lattice tubular structure.

20. The method of claim 17, further comprising the step of forming a plurality of anchor projections projecting from the anchoring end of the lattice tubular structure.

* * * * *